United States Patent [19]

Dorn et al.

[11] Patent Number: 4,927,605
[45] Date of Patent: May 22, 1990

[54] SPECIMEN COLLECTION AND SAMPLING CONTAINER

[75] Inventors: Gordon L. Dorn, Dallas; Michael A. Johnson, Fort Worth, both of Tex.

[73] Assignee: Wadley Technologies, Inc., Dallas, Tex.

[21] Appl. No.: 41,153

[22] Filed: Apr. 22, 1987

[51] Int. Cl.⁵ .............................................. G01N 1/18
[52] U.S. Cl. ................................. 422/102; 422/61;
422/68.1; 436/18; 436/176; 436/180;
73/864.22; 73/864.23; 73/864.84; 73/864.86;
128/763; 128/765; 604/411; 604/414
[58] Field of Search ................ 422/102, 100, 58, 61,
422/68; 436/18, 176, 180; 73/863.52, 863.21,
864.01, 864.22, 864.23, 864.52, 864.83, 864.84,
864.85, 864.86; 128/760, 763, 765; 604/317,
403, 411, 414, 415

[56] References Cited

U.S. PATENT DOCUMENTS

| | | | |
|---|---|---|---|
| 2,460,641 | 2/1949 | Kleiner | 128/214 |
| 2,834,346 | 5/1958 | Adams | 128/218 |
| 2,876,775 | 3/1959 | Barr, Sr. et al. | 128/272 |
| 2,880,723 | 4/1959 | Adams | 128/215 |
| 2,953,132 | 9/1960 | Richter et al. | 128/272 |
| 3,066,671 | 12/1962 | Cohen | 128/272 |
| 3,074,541 | 1/1963 | Roehr | 206/43 |
| 3,141,460 | 7/1964 | Tsochatzopoulos | 128/276 |
| 3,366,103 | 1/1968 | Keller | 128/2 |
| 3,369,708 | 2/1968 | Hein | 222/85 |
| 3,395,696 | 8/1968 | Brown et al. | 128/2 |
| 3,494,351 | 2/1970 | Horn | 128/2 |
| 3,495,591 | 2/1970 | Wilson | 128/218 |
| 3,499,327 | 3/1970 | Lane, Jr. | 73/421 |
| 3,513,829 | 5/1970 | Deuschle | 128/2 |
| 3,545,427 | 12/1970 | Ryan | 128/2 |
| 3,608,550 | 9/1971 | Stawski | 128/272 |
| 3,805,991 | 4/1974 | Cheladze | 220/44 R |
| 3,859,671 | 1/1975 | Iomasello | 215/6 |
| 3,894,845 | 7/1975 | McDonald | 23/253 R |
| 3,904,482 | 9/1975 | Mehl | 195/109 |
| 3,947,251 | 3/1976 | Quame | 23/259 |
| 3,958,572 | 5/1976 | Lawhead | 128/272 |
| 4,024,857 | 5/1977 | Blecher | 128/2 F |
| 4,063,460 | 12/1977 | Svensson | 73/425.6 |
| 4,064,760 | 12/1977 | Benjamin | 73/421 R |
| 4,116,066 | 9/1978 | Mehl | 73/421 R |
| 4,227,413 | 10/1980 | Blum | 73/421 R |
| 4,300,404 | 11/1981 | Mehl | 73/863.52 |
| 4,300,404 | 11/1981 | Mehl et al. | 73/863.52 |
| 4,577,274 | 12/1985 | Cawood | 128/760 |
| 4,610,171 | 9/1986 | Nason | 422/102 |

FOREIGN PATENT DOCUMENTS 1019500 2/1966 Fed. Rep. of Germany.
947908 1/1964 United Kingdom.

OTHER PUBLICATIONS

"A Urine Preservative System to Maintain Bacterial Counts", Goodman, et al.; Clinical Pediatrics, Jul. 1985, pp. 383–386.

Primary Examiner—Barry S. Richman
Assistant Examiner—Lynn M. Kummert
Attorney, Agent, or Firm—Richards, Medlock & Andrews

[57] ABSTRACT

The invention provides a specimen collection and sampling device, particularly useful for urine samples, for collecting a liquid sample and segregating an aliquot of the sample away from contact with the remaining portion of the sample. This segregation is accomplished as the lid is closed on the container. In one embodiment, the aliquot sample is transferred to an evacuated tube held within the container. In another embodiment, the aliquot is held within a sample chamber that is built into the container. In a preferred embodiment, the aliquot is mixed with a treating agent to maintain the microbiological integrity of the aliquot, or to provide an appropriate reagent or buffer for drug analysis.

57 Claims, 4 Drawing Sheets

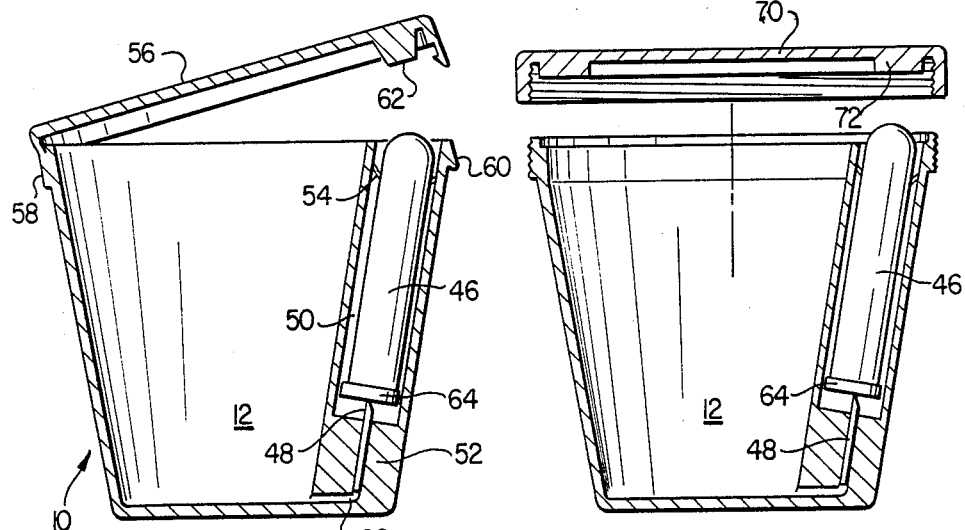
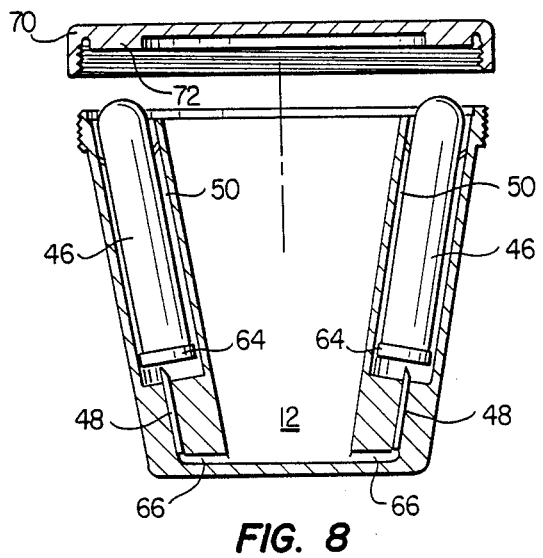

SPECIMEN COLLECTION AND SAMPLING CONTAINER

TECHNICAL FIELD

The invention relates to a specimen collection container for collection of a sample which provides means for segregating a small aliquot, or several aliquots, of the sample away from contact with the remaining portion of the sample. The aliquot portion is preferably mixed with a treating agent in order to maintain the microbial integrity of the sample in the state in which it was originally taken, or in the alternative, with other desired treating agents which allow the aliquot to be analyzed for the presence of drugs or other chemical components.

BACKGROUND ART

This invention concerns specimen collection and sampling containers for collection of liquid specimens, such as urine. At present, liquid specimens are usually collected in plastic or glass containers that may have a lid or cover to close the container. The specimens are then sent to a distant lab for analysis, or put aside until a technician is ready to initiate the analysis procedure. At the lab or testing site, portions of the sample are transferred from the collection container to other containers more suitable for use in analysis and storage of the sample such as test tubes. It is often desirable to split a specimen into several aliquots so that each aliquot may be tested for a different characteristic. For example, one aliquot may be tested for the presence of specific chemicals, enzymes, etc. and another may be tested for microorganism count or bacterial identity. Transfer of the sample from the collection container under sterile conditions is problematic. Such methods as pouring, pipetting and funneling the sample from the collection container to a test tube or other receptacle are often disadvantageous because the microbiological and chemical integrity of the original sample may be sacrificed if aseptic techniques are not followed. Additionally, the increased possibility of mislabeling occurs with each transfer leading to erroneous results for a particular patient.

Specimen collection is addressed in U.S. Pat. Nos. 4,116,066 and 4,300,404 both to Mehl, et al. Devices providing a cannula attached to a collection container and to the lid through which fluid can be transferred from the container to a separate evacuated tube are disclosed therein. These apparatus reduce the possibility of spillage or contamination of the sample during the transfer. After fluid is introduced into a collection device as described by Mehl, an operator or technician may, at a later point in time, apply an evacuated tube to the Mehl device to withdraw an aliquot. Thus, transfer of an aliquot from the collection vessel requires an additional device, an additional step and generally skilled technical assistance. Even after the transfer is accomplished, the specimen remains suspect as the time interval between collection and specimen transfer can be variable and dependent on human efficiency.

One major problem not addressed by the Mehl patents, nor any other collection device known in the art, therefore, is the time lag between the collection of the sample and the analysis of the sample. Typically, this amounts to a period of days, or at least a minimum of several hours. During this period, the microbiological integrity of the sample can change significantly thereby causing inaccurate results. Due to the importance placed particularly on urine analysis for diagnosis of disease and a determination of the presence of foreign substances in the body, fair and accurate analysis and results are absolutely critical.

Since analysis of the sample immediately after the sample is taken is almost always logistically impossible, the alternative is to preserve at least a portion of the sample in the state in which it was taken. This can be accomplished by mixing a portion of the sample with a treating agent or chemical preservative of the type disclosed in a co-pending application Ser. No. 772,954 filed September 4, 1985 and entitled, "Stabilization of Specimens for Microbial Analysis," the disclosure of which is hereby incorporated by reference. Alternatively, it may be desirable to treat an aliquot of a specimen with another treating agent to produce a desired effect useful in analysis of the sample. For example, it may be desirable to admix a urine specimen to be analyzed for drugs or other chemical components with a reagent which will produce a colorimetric change if certain drugs are present, which will neutralize the pH of urine in preparation for further tests, or which will alter some other parameter of the urine specimen to suitably prepare it for analysis.

In order to ensure that a portion of the sample is preserved in the state in which it was taken, in certain instances, the preservative must be mixed with a portion of the sample immediately after the sample is taken. In other instances, immediate admixture with the treating agent is desirable even if not required. Although a portion of the sample could be transferred by hand to a separate container and mixed with the preservative, this would be cumbersome and would require the immediate attention of a nurse or the person collecting the sample. Typically, it would be difficult to ensure that such a transfer was done promptly, accurately, and aseptically. The present invention provides a device which overcomes this problem. A device is described that collects and holds a small aliquot of the specimen separate from the remaining portion and mixes it with the treating agent without requiring any extra manipulation by the nurse or the person receiving the sample. In addition, the present invention allows a larger portion of the collected specimen to remain unaltered by the treating agent, allowing for analysis for drugs, sugar levels, or other desired parameters. In the alternative, the larger portion of the sample may also be brought in contact with a treatment admixture suitable for other purposes, e.g., chemical or enzymatic stabilization.

SUMMARY OF THE INVENTION

The invention provides a specimen sampling device, particularly useful for urine specimens, that collects a liquid specimen and segregates an aliquot of it away from the remaining portion of the specimen. Preferably, this aliquot is brought into contact with the treating agents necessary to maintain the microbial integrity of the sample from the time of specimen collection to a time of specimen analysis. The segregation of the aliquot is accomplished without manipulation by the nurse or the person receiving the sample but simply by closing a lid on the collection container after the sample is placed in the container. An aliquot of the sample is held within a separate compartment or chamber, which may be comprised of an evacuated tube, located within the container when the lid is closed. This sample portion is held in the compartment, mixed with the treating agent, and can be easily withdrawn at some later time. The separate compartment may contain any treating agent desired for admixture with an aliquot of the specimen, for example a drug testing agent or sample preparative agent such as a buffer.

More than one separate compartment for segration of specimen aliquots may be provided. Each compartment may contain a different specimen treating agent, or the same treating agent so as to allow for multi-parameter testing of a single specimen in the former case or duplicate treated aliquots in the latter.

According to one embodiment of the invention, the specimen collection container is comprised of a plastic container with a screw-on or snap-on lid. The lid holds a small vacuum tube closed by a stopper within a support chamber protruding from the lid with the stoppered end of the tube directed towards the bottom of the container. Attached to the chamber and positioned below the tube is a shaft, a portion of which is accordian-shaped, that contacts the inner bottom of the container when the lid is closed. Protruding from the top of the shaft directly below the stoppered end of the vacuum tube is a needle adapted for puncturing the stopper. Ports are located at the base of the shaft that allow fluid in the container to flow through the ports, up the shaft and into the needle. As the lid is closed on the container, the shaft is forced against the bottom of the container and the tube is forced down upon the needle. The needle punctures the stopper on the vacuum tube, and the vacuum in the tube draws fluid into the tube from the container through the ports. The vacuum tube preferably contains a treating agent that mixes with the fluid as it enters the tube. The remainder of the specimen is contained in the main portion of the container. When the aliquot specimen is ready for analysis, the tube may be removed from the container by removing a peel-off cover on the lid that covers the tube compartment. The remaining portion of the sample may be refrigerated, if desired, to await other analysis. The container may be provided with a plurality of vacuum tubes and corresponding needles and shafts so that several aliquots may be segregated from the main specimen for admixture with different treating agents, or so that multiple aliquots admixed with the same treating agent may be obtained.

As an alternative to the accordian-shaped shaft described above, the needle may be positioned on the top of a hollow column or rigid base attached to the tube chamber in a plunger-type fashion. The column or base has ports located below the needle allowing fluid to flow from the container to the needle. As the lid is closed on the container, the base of the column hits the bottom of the container, and the chamber is forced down over the column with the needle penetrating the stopper on the tube.

Another embodiment of the invention comprises a container having a channel on the inside of the container for holding the vacuum tube. The needle is positioned near the side of the container directly beneath the stoppered end of the vacuum tube. As the lid is closed on the container after the sample has been introduced into the container, the lid, or a protrusion on the lid, forces the tube down onto the needle such that it punctures the stopper, and the vacuum in the tube draws fluid from the container into the tube. A portion of the sample is thereby preserved in the tube, and the tube is easily removable by removing the lid. In order to provide a plurality of sample chambers, several tubes may be used as sample chambers with the tubes being placed in channels within the container and each tube having an associated needle to pierce the stopper on the tube. Either a screw-on lid with an appropriately located inner rim, or a snap-on lid with appropriately located protrusions may be used with the multiple tubes.

In another embodiment of the invention, a vacuum tube is attached to the lid and a needle is attached to the bottom of the cup portion of the container, such needle being positioned directly below the stoppered end of the tube as the lid is closed. The needle may be attached to a built-up base or shaft that has ports below the needle that allow fluid to enter and flow to the needle. The tube may be held within a chamber by the peel-off cover and may be removed from the container by removing the cover.

According to another embodiment of the invention, a specimen container is provided that includes a sampling chamber built into the container. The sampling chamber may lie below the main compartment of the container, or it may lie around the bottom of the inside walls of the container. The chamber is sealed off from the main compartment of the container except for one opening through which fluid may enter the chamber from the main compartment. One of several means may be used to close off this opening: a flexible piece of plastic sliding in a grooved slot, a plug that fits into the opening, a hinge, or a threaded screw. All of these closure means are activated by simply closing the lid on the container after the sample has been introduced into the container. The chemical preservative or treating agent can be placed in the sample chamber prior to the entry of the sample. The chamber may be accessed through an external port extending through the wall of the container that is adapted for easy transfer of the portion of the sample in the chamber to another container, such as an evacuated tube, for analysis.

BRIEF DESCRIPTION OF THE DRAWING

The foregoing and additional objects and advantages of the invention will be more apparent when the following detailed description is read in conjunction with the accompanying drawing, wherein like reference characters denote like parts in all views and wherein:

FIG. 6 shows another embodiment of the invention with the needle and the vacuum tube included within a channel on the inside of the container with a snap-on lid;

FIG. 7 shows the embodiment of FIG. 6 with a screw-on lid;

FIG. 8 is a side view showing a container incorporating two tubes held within channels;

DETAILED DESCRIPTION OF THE INVENTION

The present invention provides a specimen collection container that collects, segregates and holds an aliquot, or several aliquots, of a liquid sample away from contact with the remaining sample in order to preserve the microbial or chemical integrity of the aliquot. The segregation of the aliquot requires no extra manipulation as the segregation is accomplished by simply closing the lid on the container after the sample is received. Preferably, the separated portion of the sample is brought in contact with a treating agent. This reduces the possibility of the sample becoming altered due to the time lag between taking the sample and performing the analysis on the sample. The preserved sample can later be removed separately from the main portion of the sample. The invention is particularly useful in preserving a urine sample for microbiological and chemical analysis, but it can be used for similar analysis of other liquid samples as well, such as milk samples. While the preferred embodiment uses a microbial preservative to mix with the aliquot, it is envisioned that any type of chemical or biological treating agent desired may be introduced into the segregation chamber and mixed with the aliquot. For example, pH altering agents, buffers, drug analysis reagents and the like may be employed as treating agents.

Figure 1:
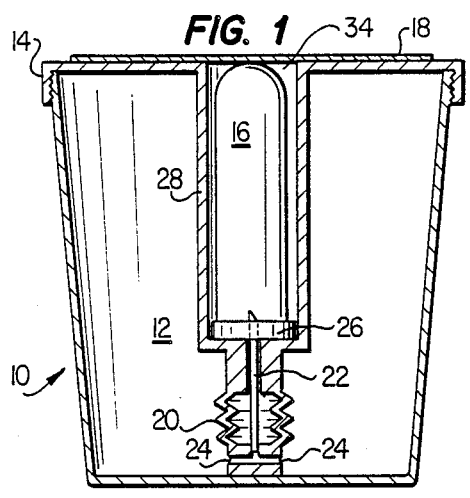
FIG. 1 is a side view of one embodiment of the specimen collection container showing a vacuum tube held by the lid with a needle protruding from an accordian-shaped shaft inserted through the stopper on the vacuum tube and the lid closed on the container.

One embodiment of the invention provides a specimen collection container that includes a small vacuum tube, about 2 ml, with a stoppered end and a needle for puncturing the stopper all held within the collection container. FIG. 1 shows one embodiment for the collection container, generally shown as 10. Container 10 is comprised of a lower cup portion 12 and a lid 14. Lid 14 may be a screw-on lid as it is shown in FIG. 1 with the associated threads on the outer rim of the cup and the inner rim of the lid. Alternatively, lid 14 may be a snap-on lid with the lid closing down over the cup and the cup having a lip or other catch means for securing the snap-on lid. Included in this embodiment is a vacuum tube 16 held within a support chamber 28 by a peel-off cover 18 which covers an access hole 34 in the lid 14. Support chamber 28 protrudes from the inner side of the lid and may be molded as one piece with the lid.

Attached to the support chamber 28, is a shaft 20 a portion of which is accordian-shaped, and the shaft holds a hollow needle 22 directly below a stopper 26 on tube 16. The accordian shape gives shaft 20 some compressibility as it contacts the bottom of the container. Near the base of shaft 20 are ports 24 that allow fluid to enter shaft 20 from cup 12. As the lid 14 is screwed down onto the cup 12, the shaft 20 is forced against the bottom of cup 12. The accordian shape of the shaft 20 allows the shaft to compress to an extent as the lid is being closed. As the lid continues to close, the needle 22 pierces the stopper 26 and the vacuum in tube 16 draws liquid from the cup 12 through the ports 24, shaft 20, needle 22 and into the tube 16. As the fluid enters the tube 16, it comes in contact with a treating agent that is contained in the tube that acts to preserve the sample in the tube in that state in which it entered. FIG. 1 shows container 10 in the closed position with the needle 22 through the stopper 26.

Figure 2:
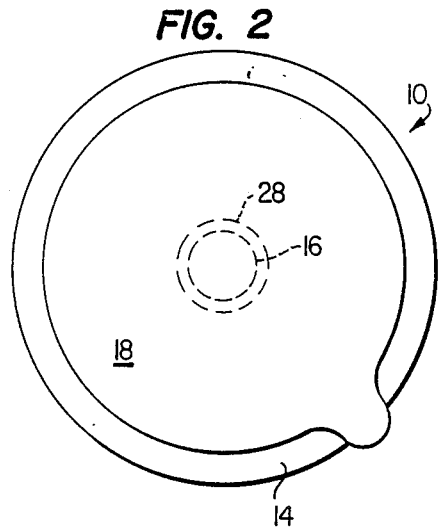
FIG. 2 is a plan view of the lid with the peel-off label holding the tube.

The peel-off cover 18 is a flexible but semirigid material, such as aluminum, paper or plastic, that is coated with an adhesive on the underside to stick to the lid 14. FIG. 2 shows a plan view of the lid 14 with the peel-off cover 18, vacuum tube 16, and the support chamber 28 for holding the tube 16. The cover 18 holds tube 16 within support chamber 28 as it is forced upward by the needle 22 before the needle pierces the stopper 26. The peel-off cover 18 covers access hole 34 in lid 14. The vacuum tube 16 may be removed from container 10 by peeling off cover 18 and removing the tube through the hole 34. The cover 18 may then be repositioned to cover the access hole 34. Access hole 34 may be enlarged to provide easier removal of tube 16.

Figure 3:
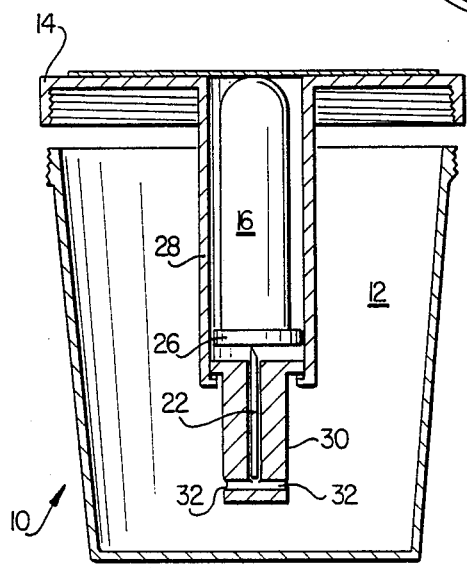
FIG. 3 is a side view of one embodiment of the invention utilizing a column support for the needle and showing the lid approaching the closed position.

As an alternative embodiment of the invention, a hollow column shaft 30 may replace the accordian shaft 20 in FIG. 1. The column 30, shown in FIG. 3, is slidably engaged with the support chamber 28 directly below tube 16 and has sample ports 32 near its base to allow fluid to enter the column and flow up through needle 22. The column 30, as well as the accordian-shaft 20 shown in FIG. 1, secures needle 22 in a substantially vertical position so that it can easily pierce the stopper 26 on tube 16. As the lid 14 is placed on the container and begins to close, the column 30 contacts the bottom of cup 12 and the chamber 28 slides over column 30. Unlike the accordian-shaped shaft in FIG. 1, when the column 30 contacts the bottom of cup 12 it does not yield but is rigid, and it forces the needle 22 through the stopper 26. Again, the tube 16 is held within support chamber 28 by a peel-off cover 18. The cover 18 may be pulled back and the tube 16 easily removed.

Figure 4:
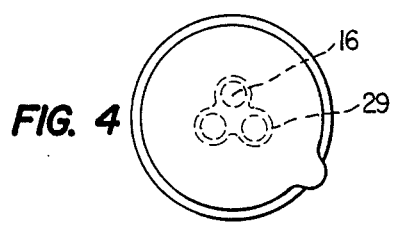
FIG. 4 is a plan view showing one embodiment of the invention that provides multiple sample chambers.

A plurality of sample chambers may be provided in order to provide a plurality of preserved samples or to treat several portions of a sample with a different treating agent for various analyses. In the embodiments shown in FIGS. 1 and 3, several evacuated tubes could be held within a chamber. FIG. 4 shows a plan view of one embodiment that includes three evacuated tubes 16 held within a chamber 29. Needles held within shafts similar to the ones shown in FIGS. 1 and 3 may be used with each tube in FIG. 4.

Figure 5:
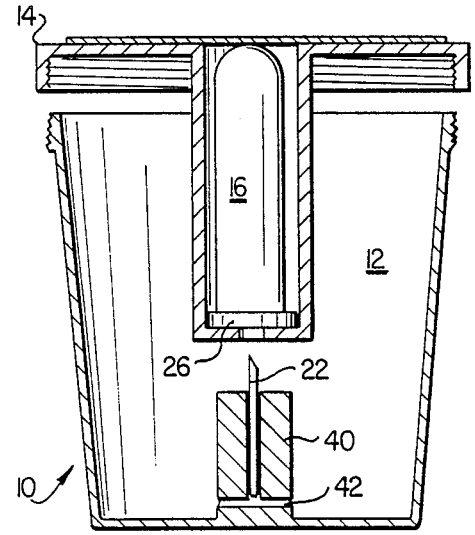
FIG. 5 is a side view of an embodiment of the invention that provides a built-up base in the container and the needle attached to the base directly below the vacuum tube as the lid is closed.

Another embodiment of the invention is shown in FIG. 5. A built-up base or support 40 is attached to the bottom of cup 12 which holds needle 22 in a substantially vertical position. Needle 22 is positioned such that it is directly below the stopper 26 of tube 16 when the lid 14 is placed on the cup 12. As before, when the lid 14 is closed, the needle 22 pierces the stopper 26 on the tube 16 and fluid in the cup 12 is drawn by the vacuum in tube 16 into the tube through ports 42 located near the base of column 40 and through the needle 22. As shown in FIG. 5, the other features of the container 10 are as described for the first and second embodiments shown in FIGS. 1 and 3.

Another embodiment of the invention is shown in FIG. 6. The vacuum tube 46 is held within a channel 50 on the inside of cup 12. Needle 48 is positioned directly below the stoppered end of vacuum tube 46 within a shaft 52 or other suitable support means. Near the base of the shaft 52 is a sample port 66 that allows fluid from inside the cup to flow into the needle 48. The tube 46 may be held in place by flexible plastic support means 54. FIG. 6 shows collection container 10 with a snap-on lid 56 that is attached to cup 12 by a hinge means 58. Lip 60 is positioned on the outside of cup 12 near the top so that it acts as a latch for lid 56 as it is closed on cup 12. Lid 56 also has a piston 62 that protrudes from the underside of lid 56 and towards the bottom of cup 12 as the lid is closed. Piston 62 acts to force the tube 46 down onto the needle 48 as the lid 56 is closed on cup 12. Needle 48 pierces the stopper 64 on tube 46 and the vacuum in the tube draws fluid into the tube from the container through port 66 and needle 48. A treating agent may be introduced into the tube 46 prior to it being positioned in channel 50 that mixes with the sample fluid as it enters tube 46. Tube 46 may be withdrawn at a later time by removing the lid and retracting the tube.

FIG. 7 shows a similar embodiment to that described in FIG. 6 except that a screw-on lid 70 is used instead of a snap-on lid. In order to accommodate lid 70, cup 12 has threads around its outer upper rim that accommodate the inner threads of lid 70. Lid 70 also has an inner rim 72 that fits inside of cup 12. As lid 70 is screwed down onto cup 12, rim 72 contacts the upper end of vacuum tube 46 and forces it down upon the needle 48. As the needle 48 punctures the stopper 64, fluid from the cup 12 is drawn into the tube 46. Similar to previously described embodiments, a treating agent may be used to treat the sample, and the tube may be removed at some later time by unscrewing the lid 70.

FIG. 8 shows an embodiment with two evacuated tubes 46 held within two channels 50 similar to the embodiments shown in FIGS. 6 and 7. More than two tubes could be arranged within the cup 12 to provide a plurality of segregated samples. FIG. 8 shows a screw-on lid with an inner rim similar to that shown in FIG. 7. A snap-on lid could also be used with the lid having protrusions located so as to force the tubes down onto the needles as the lid is closed.

Figure 9:
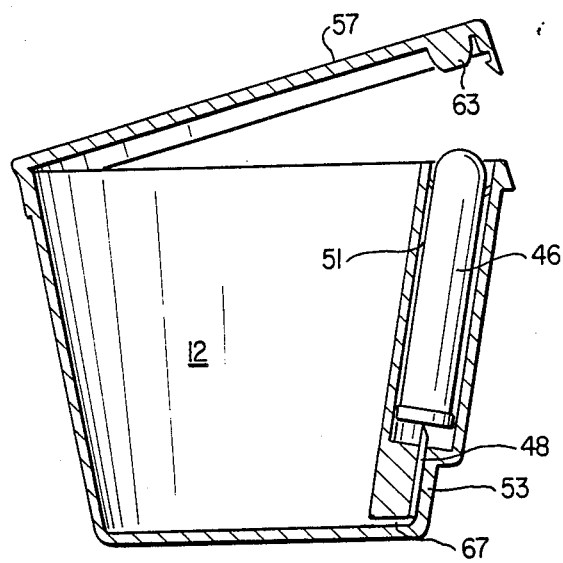
FIG. 9 is a side view showing an evacuated tube held within a channel that is formed on the outside of the container, and the container having a hinged lid.

FIG. 9 shows an evacuated tube 46 held within a channel 51 similar to that shown in FIG. 6, but the channel 51 is formed on the outside of the cup 12. Sample passage 67 allows fluid from inside the cup 12 to flow to the needle 48 which is held by a support 53. A snap-on lid 57 with a protrusion 63 is used to force the tube down onto the needle. Similarly, a screw-on lid could be used with a rim extending from the lid so as to force the tube down onto the needle as the lid is screwed on the cup. Also, a plurality of tubes could be used and arranged in channels around the outside of the cup.

Figure 10:
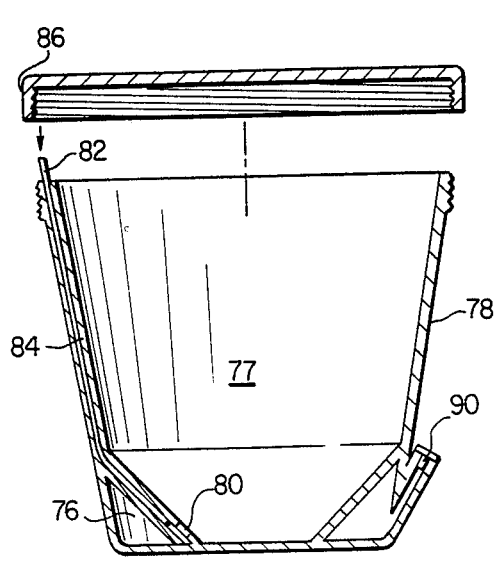
FIG. 10 shows another embodiment of the invention with a sampling chamber around the bottom of the inside walls of the container with one opening into the main compartment, an external sample port and closure means that uses a sliding piece of flexible plastic in a grooved slot.

According to another embodiment of the invention, a sampling chamber is built into the cup portion of the container with an opening to the main chamber that may be closed by various alternative means as the lid is closed on the container. FIG. 10 shows one embodiment of the invention that includes a sample chamber 76 positioned around the base of the walls of the cup 78. The chamber 76 has an opening 80 which allows fluid to enter the chamber from the main compartment 77 of cup 78. A flexible strip of plastic 82 sliding in a grooved slot 84 acts as a closure means for closing the opening 80. The flexible piece of plastic 82 and the grooved slot 84 extend from the bottom of the cup 78 where it closes opening 80 along the side and up to the top of cup 78. The closure means are activated, as before, by closing the lid on the container. As the lid 86 is screwed onto cup 78, the inner side of lid 86 contacts the upper end of the plastic strip 82 and forces it in slot 84 down towards the bottom of cup 78 and over opening 80. Plastic strip 82 is proportioned such that as lid 86 is tightened down on cup 78, strip 82 has completely covered opening 80 and closed off the flow of fluid from the main compartment 77 to the sample chamber 76. Cup 78 has an external sample port 90 that extends from sample chamber 76 through the wall of cup 78 and protrudes beyond the cup. The sample port 90 is adapted to allow for easy transfer of the sample in chamber 76 to an appropriate testing vessel such as a test tube. A treating agent may be introduced into the sample chamber 76 via the sample port 90 in a tablet or capsule form before a sample is introduced into the container and the sample port closed.

Figure 11:
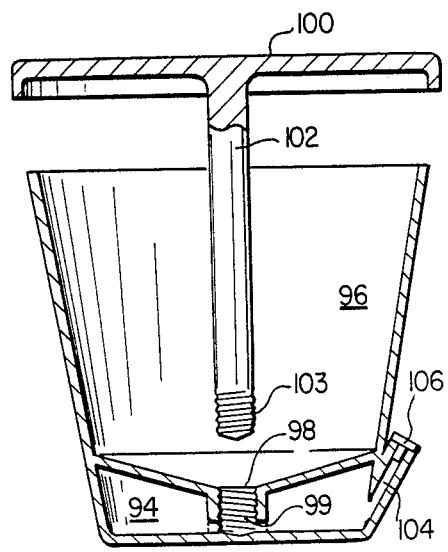
FIG. 11 shows one embodiment of the invention that has a sample chamber below the bottom of the main compartment with an external sample port and threaded screw closure means.

Another embodiment of the invention is shown in FIG. 11. In this embodiment, a sample chamber 94 is built into the bottom of cup 96 such that it is below the main compartment of cup 96. Chamber 94 has an opening 98 near the center which is fitted with receiving threads 99. As shown in FIG. 11, lid 100 includes a protrusion 102 extending from the lid 100 into the opening 98 when the lid is closed on the container. The end of protrusion 102 has external threads 103 that fit the threads 99 of opening 98. As lid 100 is screwed onto cup 96, the protrusion 102 screws into the opening 98 and closes off the flow of fluid between the sample chamber 94 and the main compartment of the cup 96 and holds lid 100 securely closed upon cup 96. FIG. 11 shows a similar configuration for an external sample port 104 to that shown in FIG. 10. After the lid 100 is closed, the fluid in chamber 94 may be accessed through sample port 104 by removing stopper 106 or by syringe through the stopper. Again, a treating agent may be placed in the chamber 94 through the sample port 104 before the stopper is put in place and before the sample is introduced into the container.

Figure 12:
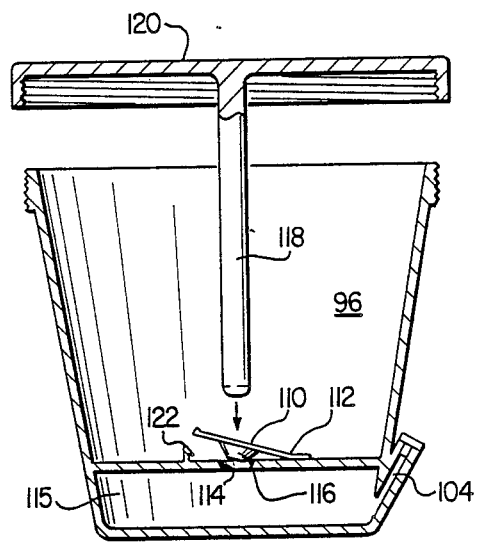
FIG. 12 shows a container with a sampling chamber and hinged closure means.

FIG. 12 shows an alternative embodiment to that shown in FIG. 11. Instead of threaded closure means, the embodiment in FIG. 12 includes a hinged closure flap 110 attached to the bottom of the main compartment of cup 96 by a hinge 112. The flap 110 is positioned above an opening 114 and has a plug 116 which helps to plug opening 114. A protrusion 118 from lid 120 forces flap 110 down against plug 116 to cover opening 114 as the lid 120 is screwed down onto the container. As the flap 110 is forced down over opening 114, a catch 122 positioned adjacent to flap 110 will catch and hold the flap in the closed position. Catch 122 is somewhat flexible as it is bent slightly as flap 110 is closed, but then catch 122 returns to its upright position to hold flap 110. Flap 110 is also adapted to effectively seal off the opening 114 when the flap is in the closed position. Again, the sample in chamber 115 may be accessed through external sample port 104, and a treating agent may be introduced as previously described.

Figure 13:
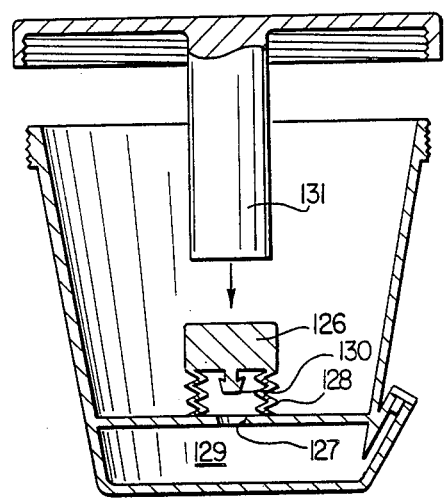
FIG. 13 shows a container with a plug for closing the sample chamber.
Figure 14:
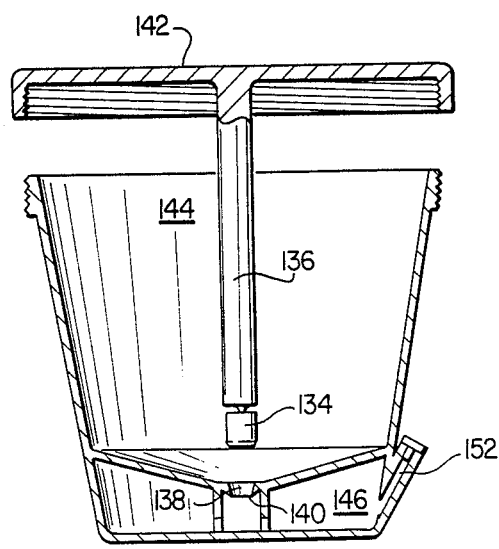
FIG. 14 shows a break-away plug with catch means.
Figure 15:
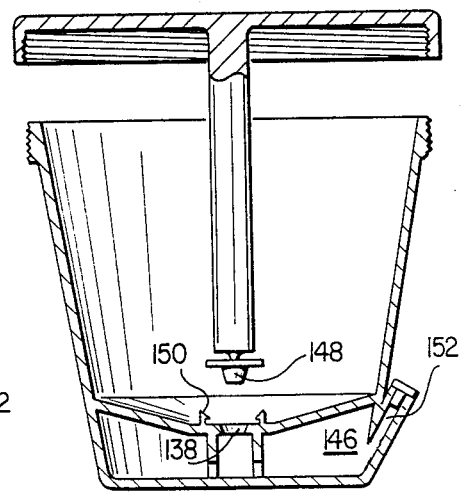
FIG. 15 shows another embodiment of a breakaway plug with catch means.

FIGS. 13, 14 and 15 show other alternative closure means to those described in FIGS. 11 and 12. FIG. 13 shows a plug 126 attached to the bottom of the main compartment of cup 96 by an accordian shaped support 128 that is compressible with the plug 126 being positioned directly above an opening 127. The support 128 has openings that allow fluid to enter the sample chamber 129 from the main compartment of the container when the plug is in the open position. The plug 126 has tabs 130 that lock the plug 126 in the opening 127 once plug 126 has been forced into the closed position. Plug 126 is closed by a protrusion 131 that forces the plug into the opening 127 as the lid is closed on the container.

Another embodiment for the plug closure means is shown in FIG. 14 as a break-away plug 134 is attached to the end of protrusion 136. Within an opening 138 are catches 140. When the lid 142 is screwed onto the cup 144, the rubber plug 134 is pressed into the opening 138 thereby sealing off a sample chamber 146. The catches 140 hold the plug 134 in place, and the plug 134 breaks off of protrusion 136 when the lid is removed. FIG. 15 shows another embodiment for a break-away plug 148 with the catch means 150 located adjacent to the opening 138. Again, an external sample port 152 provides access to the sample chamber 146 for introducing a preservative and withdrawing the sample from chamber 146. Similarly, other devices may be used to close opening 138.

From the foregoing detailed description, it is apparent that the invention describes a specimen sampling device that collects a liquid sample and segregates an aliquot of the sample from the remaining portion of the sample so that it may be treated by mixing it with an appropriate treating agent. This segregation is accomplished by simply closing the lid on the collection container. Having described only a few embodiments, it will be apparent to those skilled in the art that various modifications may be made to the invention as described without departing from the spirit of the invention.

What is claimed:
1. A specimen collection container comprising:
 a cup positioned and arranged to receive and hold a specimen, the cup having an open top end and a closed bottom end;
 a lid positioned and arranged to engage securely with the open top end of the cup,
 a main compartment contained within the cup,
 at least one sample chamber attached to said container, the at least one sample chamber positioned and arranged to receive an aliquot of specimen from said main compartment;
 segregation means for segregating the aliquot into the at least one sample chamber as the lid is closed onto the cup, the segregation means preventing fluid flow between the main compartment and the at least one sample chamber when said aliquot of specimen is being removed from the at least one sample chamber;
 a support chamber projecting from the lid, inside the cup and towards the bottom end of the cup when the lid is placed on the cup, an evacuated tube being held within said support chamber; and
 an accordion-shaped shaft connected to the support chamber and holding a needle, the shaft contacting the bottom of the cup when the lid is closed on the cup.

2. A specimen collection container comprising:
 a cup positioned and arranged to receive and hold a specimen, the cup having an open top end and a closed bottom end;
 a lid positioned and arranged to engage securely with the open top end of the cup,
 a main compartment contained within the cup,
 at least one sample chamber attached to said container, the at least one sample chamber positioned and arranged to receive an aliquot of specimen from said main compartment;
 segregation means for segregating the aliquot into the at least one sample chamber as the lid is closed onto the cup, the segregation means preventing fluid flow between the main compartment and the at least one sample chamber when said aliquot of specimen is being removed from the at least one sample chamber;
 a support chamber projecting from the lid, inside the cup and towards the bottom end of the cup when the lid is placed on the cup, an evacuated tube being held within said support chamber and having a stopped end; and
 a compressible shaft with a needle mounted on the shaft with the needle being positioned and arranged to pierce the stoppered end of the evacuated tube as the lid is closed on the cup, the shaft being connected to the support chamber and being compressible as the shaft contacts the bottom of the cup when the lid is closed on the cup, and the shaft having ports near the base of the shaft for receiving liquid from the main compartment and allowing the liquid to flow up to the needle.

3. The container of claims 1 or 2 wherein the lid defines an access hole for enabling removal of the evacuated tube from the support chamber with the lid closed on the cup.

4. The container of claim 3 further comprising a peel-off cover for covering the access hole and holding the evacuated tube in the support chamber.

5. The container of claim 4 wherein the peel-off cover is a flexible semi-rigid material that is coated with an adhesive to enable the peel-off cover to stick to the lid.

6. The container of claims 1 or 2 wherein the lid is a snap-on lid, the snap-on lid having closure means for securing the snap-on lid closed upon the cup.

7. The container of claims 1 or 2 wherein the lid is a screw-on lid with the screw-on lid having threads that mate with threads on the cup.

8. A specimen collection container comprising:
 a cup positioned and arranged to receive and hold a specimen, the cup having an open top end and a closed bottom end;
 a lid positioned and arranged to engage securely with the open top end of the cup,
 a main compartment contained within the cup,
 at least one sample chamber attached to said container, the at least one sample chamber positioned and arranged to receive an aliquot of specimen from said main compartment;
 segregation means for segregating the aliquot into the at least one sample chamber as the lid is closed onto the cup, the segregation means preventing fluid flow between the main compartment and the at least one sample chamber when said aliquot of specimen is being removed from the at least one sample chamber; and a support chamber projecting from the lid, inside the cup and towards the bottom end of the cup when the lid is placed on the cup, an evacuated tube being held within said support chamber and having a stoppered end;

a needle support means for positioning a needle below the stoppered end of the evacuated tube when the lid is placed on the cup, the needle support means being connected to the support chamber, the needle support means having ports that allow fluid to flow from the main compartment into the needle, and the needle support means being slidably engaged with the support chamber.

9. The container of claim 8 wherein the needle support means is a column support connected to the support chamber, the needle being attached in a substantially vertical position to said column support, the column support having ports near the base of said column support for receiving fluid from the main compartment and allowing the fluid to flow up to the needle, the column support being positioned below the stoppered end of the evacuated tube and contacting the bottom of the cup when the lid is closed on the cup.

10. A specimen collection container comprising:
a cup positioned and arranged to receive and hold a specimen, the cup having an open top end and a closed bottom end;
a lid positioned and arranged to engage securely with the open top end of the cup,
a main compartment contained within the cup,
at least one sample chamber attached to said container, the at least one sample chamber positioned and arranged to receive an aliquot of specimen from said main compartment;
segregation means for segregating the aliquot into the at least one sample chamber as the lid is closed onto the cup, the segregation means preventing fluid flow between the main compartment and the at least one sample chamber when said aliquot of specimen is being removed from the at least one sample chamber;
a support chamber projecting from the lid, inside the cup and towards the bottom end of the cup when the lid is placed on the cup, an evacuated tube being held within said support chamber and having a stoppered end;
a needle support means for positioning a needle below the stoppered end of the evacuated tube when the lid is placed on the cup, the needle support means being connected to the support chamber and the needle support means having ports that allow fluid to flow from the main compartment into the needle; and
wherein the lid has a portion defining an access hole through which the evacuated tube may be removed with the lid closed on the cup, and the access hole being covered with a peel-off cover that holds the evacuated tube within the support chamber.

11. The container of claim 10 wherein the lid is a snap-on lid, the snap-on lid having closure means for securing the snap-on lid to the cup, and the snap-on lid further comprising a piston protruding from the snap-on lid positioned to force the evacuated tube onto the needle as the snap-on lid is snapped closed on the cup.

12. The container of claim 10 wherein the lid is a screw-on lid having threads that mate with threads on the cup, the screw-on lid further comprising an inner rim that contacts the upper end of the evacuated tube and forces the evacuated tube down onto the needle as the screw-on lid is screwed onto the cup.

13. A specimen collection container comprising:
a cup positioned and arranged to receive and hold a specimen, the cup having an open top end and a closed bottom end;
a lid positioned and arranged to engage securely with the open top end of the cup;
a main compartment contained within the cup;
a plurality of sample chambers attached to said container, the plurality of sample chambers positioned and arranged to receive an aliquot of specimen from said main compartment; and
segregation means for segregating the aliquot into the plurality of sample chambers as the lid is closed onto the cup, the segregation means preventing fluid flow between the main compartment and the plurality of sample chambers when said aliquot of specimen is being removed from the plurality of sample chambers.

14. A specimen collection container comprising:
a cup positioned and arranged to receive and hold a specimen, the cup having an open top end and a closed bottom end;
a lid positioned and arranged to engage securely with the open top end of the cup;
a main compartment contained within the cup;
a support chamber projecting from the lid, inside the cup and towards the bottom end of the cup when the lid is placed on the cup;
a plurality of evacuated tubes held within said support chamber, the evacuated tubes positioned and arranged to receive an aliquot of specimen from the main compartment; and
segregation means for segregating the aliquot into the evacuated tubes as the lid is closed onto the cup, the segregation means preventing fluid flow between the main compartment and the evacuated tubes when said aliquot of specimen is being removed from the sample chamber.

15. A specimen collection container, comprising:
a cup positioned and arranged to receive and hold a specimen, the cup having an open top end and a closed bottom end;
a lid positioned and arranged to engage securely with the open top end of the cup;
a main compartment contained within the cup;
at least one sample chamber attached to said container, the at least one sample chamber positioned and arranged to receive an aliquot of specimen from said main compartment; and
segregation means for segregation the aliquot into the at least one sample chamber as the lid is closed onto the cup, the segregation means preventing fluid flow between the main compartment and the at least one sample chamber when said aliquot of specimen is being removed from the at least one sample chamber;
wherein the at least one sample chamber is a separate chamber built into the cup with a passage to allow fluid to enter the at least one sample chamber from the main compartment;

wherein the at least one sample chamber is located around the bottom end of the inside surface of the cup;

wherein the segregation means comprises a flexible plastic strip slideably engaged within a grooved slot on a side of the cup with the passage opening to the at least one sample chamber located near a base of the slot, the plastic strip extending up the wall of the cup to the top of the cup, whereby, upon closing the lid upon the cup, the lid contacts the plastic strip and forces the plastic strip down within the slot so as to cover the passage opening to the at least one sample chamber.

16. The container of claim 15 wherein the cup wall defines an external sample port in fluid communication with the at least one sample chamber and through which fluid from the at least one sample chamber may be withdrawn.

17. A specimen collection container comprising:
a cup positioned and arranged to receive and hold a specimen, the cup having an open top end and a closed bottom end;
a lid positioned and arranged to engage securely with the open top end of the cup,
a main compartment contained within the cup,
at least one sample chamber attached to said container, the at least one sample chamber positioned and arranged to receive an aliquot of specimen from said main compartment; and
segregation means for segregating the aliquot into the at least one sample chamber as the lid is closed onto the cup, the segregation means preventing fluid flow between the main compartment and the at least one sample chamber when said aliquot of specimen is being removed from the at least one sample chamber;
wherein the at least one sample chamber is a separate chamber built into the cup with a passage to allow fluid to enter the at least one sample chamber from the main compartment;
wherein the at least one sample chamber is built into the cup below the main compartment of the cup, and further comprising an external sample port in fluid communication with the at least one sample chamber through which fluid from the at least one sample chamber may be withdrawn;
a protrusion extending from the lid towards the bottom of the cup and the protrusion operating to close the passage opening to the at least one sample chamber as the lid is closed on the cup thereby sealing off the flow of fluid from the main compartment to the at least one sample chamber.

18. The container of claim 17 wherein the protrusion operates to close the opening by the end of the protrusion screwing into a threaded opening as the lid is screwed onto the cup, the end of the protrusion having threaded sides that fit with the threaded opening.

19. The container of claim 17 further comprising a hinged flap attached to the bottom of the main compartment that covers the passage opening to the at least one sample chamber when the flap is in a closed position, and wherein the flap is forced into the closed position by said protrusion as the lid is closed on the cup.

20. The container of claim 19 further comprising catch means for holding the hinged flap in the closed position once the hinged flap has been positioned to cover the passage opening.

21. The container of claim 17 further comprising a plug connected to a compressible support means which is connected to the bottom end of the main compartment and the plug being positioned above the passage opening to the at least one sample chamber such that when the lid is closed on the cup the protrusion from the lid contacts the plug and forces the plug into the passage opening thereby sealing off the flow of fluid into the at least one sample chamber.

22. The container of claim 21 further comprising tabs on the plug that hold the plug in place once the plug has been introduced into the passage opening.

23. The container of claim 17 further comprising a break-away plug connected to the protrusion, such that as the lid is closed on the cup, the protrusion forces the break-away plug into the passage opening thereby sealing off the flow of fluid to the at least one sample chamber, the plug being attached to the protrusion in such a way that the plug breaks off from the protrusion as the lid is removed and the protrusion withdrawn.

24. The container of claim 23 further comprising catch means for retaining the plug in the passage opening once the plug has been introduced into the opening.

25. A urine collection container comprising:
a cup positioned and arranged to receive and hold a specimen, the cup having an open top end and a closed bottom end,
a lid positioned and arranged to engage securely with the open top end of the cup;
a support chamber attached to the underside of the lid that projects towards the bottom end of the cup when the lid is closed onto the cup,
an evacuated tube with a stoppered end, the evacuated tube being held within the support chamber with the stoppered end of the evacuated tube directed towards the bottom end of the cup as the lid is closed on the cup,
a shaft connected to the support chamber such that the shaft contacts the bottom end of the cup as the lid is closed on the cup, and the shaft having ports near the base of the shaft, and
a hollow needle attached to the shaft, the needle having one end positioned and arranged for piercing the stopper on the evacuated tube, and the one end being positioned directly below the stoppered end of the evacuated tube held in the support chamber as the lid is closed on the cup, the needle being in fluid communication with the ports of the shaft,
whereby, as the lid is closed on the cup, the shaft is forced against the bottom of the cup and the stoppered end of the evacuated tube is forced down upon the needle and the needle pierces the stoppered end of the evacuated tube thereby drawing fluid from the cup into the evacuated tube; wherein the lid defines an access hole for removing the evacuated tube from the cup when the lid closes on the cup, and the access hole being covered with a flexible, semi-rigid, peel-off cover that may be removed in order to remove the evacuated tube.

26. The container of claim 25 wherein a portion of the shaft is a compressible, accordion-shaped shaft.

27. The container of claim 25 wherein the shaft is a rigid column.

28. The container of claim 25 wherein the lid is a screw-on lid with closure means comprising a threaded lid on the outer surface of the open end of the cup and mating threads on the inner surface of the rim of the lid.

29. A urine collection container comprising:
a cup positioned and arranged to receive and hold a specimen, the cup having an open top end and a closed bottom end,
a lid with closure means for securing the lid onto the cup,
means defining a channel attached to the cup,
an evacuated tube with a stoppered end held within the means defining a channel with the stoppered end directed towards the bottom end of the cup,
a needle positioned and arranged for piercing the stoppered end of the evacuated tube, the needle attached to the means defining a channel or to the cup and positioned immediately below the stoppered end of the evacuated tube, and the needle being in fluid communication with the interior of the cup, and
a protrusion extending from the lid for forcing the evacuated tube down onto the needle such that the needle pierces the stoppered end of the evacuated tube when the lid is closed on the cup.

30. The container of claim 29 wherein the lid is a screw-on lid with associated threads on the inner rim of the lid and on the outer surface of the cup, and wherein the protrusion on the lid is an inner rim that projects into the interior of the cup when the lid is closed onto the cup.

31. A urine collection container comprising:
a cup positioned and arranged to receive and hold a specimen, the cup having an open top end and a closed bottom end;
a lid with closure means for securing the lid onto the cup;
means defining a channel attached to the cup;
an evacuated tube with a stoppered end held within the means defining a channel with the stoppered end directed towards the bottom end of the cup;
a needle positioned and arranged for piercing the stoppered end of the evacuated tube, the needle attached to the means defining a channel or to the cup and positioned immediately below the stoppered end of the evacuated tube, and the needle being in fluid communication with the interior of the cup;
a protrusion extending from the lid for forcing the evacuated tube down onto the needle such that the needle pierces the stoppered end of the evacuated tube when the lid is closed on the cup; and
wherein the lid is a snap-on lid and wherein the protrusion on the lid is a piston-like protrusion that contacts an upper end of the evacuated tube and forces the evacuated tube down onto the needle as the lid is closed.

32. A urine collection container comprising:
a cup positioned and arranged to receive and hold a specimen, the cup having an open top end and a closed bottom end;
a lid positioned and arranged to fit securely onto the open end of the cup to close the cup;
a main compartment in the cup for receiving and holding a specimen;
a sample chamber built into the cup having a passage that allows fluid to enter the sample chamber from the main compartment;
an external sample port in fluid communication with the sample chambe, the external sample port positioned and arranged to allow for fluid to be withdrawn from the sample chamber; and
closure means for closing the passage opening to the sample chamber as the lid is closed on the cup.

33. The container of claim 32 wherein the closure means comprises a flexible strip slideably engaged within a grooved slot, an upper end of the strip contacting the lid as the lid is closed on the cup and being forced down so as to cover the passage opening.

34. A urine collection container comprising:
a cup positioned and arranged to receive and hold a specimen, the cup having an open top end and a closed bottom end;
a lid positioned and arranged to fit securely onto the open end of the cup to close the cup;
a main compartment in the cup for receiving and holding a specimen;
a sample chamber built into the cup having a passage that allows fluid to enter the sample chamber from the main compartment;
an external sample port in fluid communication with the sample chamber, the external sample port positioned and arranged to allow for fluid to be withdrawn from the sample chamber;
closure means for closing the passage opening to the sample chamber as the lid is closed on the cup; and
wherein the closure means comprises a protrusion extending from the lid that has a threaded end and wherein the passage opening to the sample chamber is threaded to receive the threaded end of the protrusion as the lid is closed on the cup.

35. A urine collection container comprising:
a cup positioned and arranged to receive and hold a specimen, the cup having an open top end and a closed bottom end;
a lid positioned and arranged to fit securely onto the open end of the cup to close the cup;
a main compartment in the cup for receiving and holding a specimen;
a sample chamber built into the cup having a passage that allows fluid to enter the sample chamber from the main compartment;
an external sample port in fluid communication with the sample chamber, the external sample port positioned and arranged to allow for fluid to be withdrawn from the sample chamber;
closure means for closing the passage opening to the sample chamber as the lid is closed on the cup; and
wherein the closure means comprises a protrusion extending from the lid and a hinged flap attached to the bottom of the cup near the passage opening such that as the lid is closed on the cup, the protrusion forces the hinged flap down over the passage opening so as to close the opening.

36. The container of claim 35 further comprising catch means for holding the hinged flap in the closed position once the hinged flap has been so positioned.

37. A urine collection container comprising:
a cup positioned and arranged to receive and hold a specimen, the cup having an open top end and a closed bottom end;
a lid positioned and arranged to fit securely onto the open end of the cup to close the cup;
a main compartment in the cup for receiving and holding a specimen;
a sample chamber built into the cup having a passage that allows fluid to enter the sample chamber from the main compartment;
an external sample port in fluid communication with the sample chamber, the external sample port positioned and arranged to allow for fluid to be withdrawn from the sample chamber;

closure means for closing the passage opening to the sample chamber as the lid is closed on the cup; and wherein the closure means comprises a protrusion extending from the lid and a plug attached by support means to the cup and positioned above the passage opening such that as the lid is closed on the cup, the protrusion forces the plug down into the passage opening.

38. The container of claim 37 further comprising the plug having tabs that secure the plug in the passage opening once the plug has been positioned in the opening.

39. A urine collection container comprising:
a cup positioned and arranged to receive and hold a specimen, the cup having an open top end and a closed bottom end;
a lid positioned and arranged to fit securely onto the open end of the cup to close the cup;
a main compartment in the cup for receiving and holding a specimen;
a sample chamber built into the cup having a passage that allows fluid to enter the sample chamber from the main compartment;
an external sample port in fluid communication with the sample chamber, the external sample port positioned and arranged to allow for fluid to be withdrawn from the sample chamber;
closure means for closing the passage opening to the sample chamber as the lid is closed on the cup; and
wherein the closure means comprises a break-away plug attached to a protrusion extending from the lid such that as the lid is closed on the cup, the protrusion forces the plug into the passage opening.

40. The container of claim 39 further comprising catch means that retain the plug in the passage opening once the plug is positioned in the opening.

41. An article of manufacture comprising:
a cup positioned and arranged to receive and hold a specimen, the cup having an open top end and a closed bottom end;
a lid positioned and arranged to engage securely with the open top end of the cup;
a main compartment contained within the cup;
at least one sample chamber attached to the article of manufacture, the at least one sample chamber positioned and arranged to receive an aliquot of specimen from the main compartment;
segregation means for segregating said aliquot into the at least one sample chamber as the lid is closed onto the cup, the segregation means preventing fluid flow between the main compartment and the at least one sample chamber when the aliquot of specimen is being removed from the at least one sample chamber; and
wherein the at least one sample chamber further comprises a treating agent contained within the at least one sample chamber for admixture with the specimen.

42. An article of manufacture in accordance with claim 41 wherein the treating agent is a preservative effective for maintaining the microbial integrity from a time of specimen collection to a time of specimen analysis.

43. An article of manufacture in accordance with claim 42 wherein the treating agent is a pH altering substance.

44. An article of manufacture in accordance with claim 43 wherein the pH altering substance is a buffer effective for maintaining the pH at a desired level.

45. An article of manufacture in accordance with claim 41 wherein the treating agent is a reagent effective for detecting the presence of a chemical component upon admixture with the specimen.

46. An article of manufacture in accordance with claim 45 wherein the reagent is effective for detecting a drug.

47. An article of manufacture comprising:
a cup positioned and arranged to receive and hold a specimen, the cup having an open top end and a closed bottom end,
a lid positioned and arranged to engage securely with the open top end of the cup;
a support chamber attached to the underside of the lid that projects towards the bottom end of the cup when the lid is closed onto the cup,
an evacuated tube with a stoppered end, the evacuated tube being held within the support chamber with the stoppered end of the evacuated tube directed towards the bottom end of the cup as the lid is closed on the cup;
a shaft connected to the support chamber such that the shaft contacts the bottom of the cup as the lid is closed on the cup, and the shaft having ports near a base of the shaft, and
a hollow needle attached to the shaft, the needle having one end positioned and arranged for piercing the stopper on the evacuated tube, and said one end being positioned directly below the stoppered end of the evacuated tube held in the support chamber as the lid is closed on the cup, the needle being in fluid communication with the ports of the shaft,
whereby, as the lid is closed on the cup, the shaft is forced against the bottom end of the cup and the stoppered end of the evacuated tube is forced down upon the needle and the needle pierces the stoppered end of the evacuated tube thereby drawing fluid from the cup into the evacuated tube;
wherein the evacuated tube contains a treating agent for admixture with the specimen.

48. An article of manufacture in accordance with claim 47 wherein the treating agent is a preservative effective for maintaining the microbial integrity from a time of specimen collection to a time of specimen analysis.

49. An article of manufacture in accordance with claim 47 wherein the treating agent is a reagent effective for detecting the presence of a drug upon admixture with the specimen.

50. An article of manufacture comprising:
a cup positioned and arranged to receive and hold a specimen, the cup having an open top end and a closed bottom end,
a lid with closure means for securing the lid onto the cup, means defining a channel attached to the cup, and an evacuated tube with a stoppered end held within the means defining a channel with the stoppered end directed towards the bottom end of the cup,
a needle positioned and arranged for piercing the stoppered end of the evacuated tube, the needle being positioned immediately below the stoppered end of the evacuated tube, and the needle being in fluid communication with the interior of the cup, and a protrusion extending from the lid for forcing the evacuated tube down onto the needle such that the needle pierces the stoppered end of the evacuated tube when the lid is closed on the container cup;

wherein the evacuated tube contains a treating agent for admixture with the specimen.

51. An article of manufacture in accordance with claim 50 wherein said treating agent is a preservative effective for maintaining the microbial integrity from a time of specimen collection to a time of specimen analysis.

52. An article of manufacture in accordance with claim 50 wherein said treating agent is a reagent effective for detecting the presence of a drug upon admixture with the specimen.

53. An article of manufacture comprising:

a cup positioned and arranged to receive and hold a specimen, the cup having an open top end and a closed bottom end;

a lid positioned and arranged to fit securely onto the open end of the cup to close the cup;

a main compartment in the cup for receiving and holding a specimen;

a sample chamber built into the cup having a passage that allows fluid to enter the sample chamber from the main compartment;

an external sample port in fluid communication with sample chamber, the external sample port positioned and arranged to allow for fluid to be withdrawn from the sample chamber; and closure means for closing the passage opening to the sample chamber as the lid is closed on the cup;

wherein the sample chamber further comprises a treating agent for admixture with the specimen.

54. An article of manufacture in accordance with claim 53 wherein the treating agent is a preservative effective for maintaining the microbial integrity from a time of specimen collection to a time of specimen analysis.

55. An article of manufacture in accordance with claim 53 wherein the treating agent is a reagent effective for detecting the presence of a drug upon admixture with the specimen.

56. An article of manufacture in accordance with claim 53 wherein the treating agent is a pH altering substance.

57. An article of manufacture in accordance with claim 56 wherein the pH altering substance is a buffer effective for maintaining the pH at a desired level.

* * * * *